(12) United States Patent
Dahl et al.

(10) Patent No.: US 6,368,865 B1
(45) Date of Patent: Apr. 9, 2002

(54) COMBINATORIAL PROCESS FOR PERFORMING CATALYTIC CHEMICAL REACTIONS

(75) Inventors: Ivar M. Dahl; Arne Karlsson; Duncan E. Akporiaye; Rune Wendelbo, all of Oslo (NO); Kurt M. Vanden Bussche, Lake-In-The-Hills; Gavin P. Towler, Barrington, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/464,306

(22) Filed: Dec. 15, 1999

(51) Int. Cl.$^7$ ............................................. G01N 31/10
(52) U.S. Cl. ........................ 436/37; 436/34; 436/155; 436/159; 436/161; 436/173; 422/101; 422/102
(58) Field of Search ............................ 422/82, 12, 99, 422/101–104, 130, 139; 436/34, 37, 155, 159, 161, 173

(56) References Cited

U.S. PATENT DOCUMENTS

| | | | |
|---|---|---|---|
| 3,431,077 A | * 3/1969 | Danforth | |
| 4,014,657 A | 3/1977 | Gryaznov et al. | 23/288 R |
| 4,099,923 A | * 7/1978 | Milberger | |
| 4,962,044 A | * 10/1990 | Knesel, Jr. et al. | 436/177 |
| 5,112,574 A | 5/1992 | Horton | 422/102 |
| 5,304,354 A | 4/1994 | Finley et al. | 422/196 |
| 5,405,586 A | 4/1995 | Koves | 422/218 |
| 5,425,921 A | * 6/1995 | Coakley et al. | 422/102 |
| 5,489,726 A | 2/1996 | Huss, Jr. et al. | 585/671 |
| 5,609,826 A | 3/1997 | Cargill et al. | 422/99 |

(List continued on next page.)

FOREIGN PATENT DOCUMENTS

| | | | |
|---|---|---|---|
| JP | 62-87240 | * 4/1987 | |
| WO | WO96/11878 A1 | 4/1996 | |
| WO | WO97/30784 A1 | 8/1997 | B01J/19/00 |
| WO | WO97/32208 A1 | 9/1997 | |
| WO | WO98/07026 A1 | 2/1998 | G01N/31/10 |
| WO | WO98/36826 A1 | 8/1998 | |
| WO | WO98/39099 | 9/1998 | B01L/3/00 |
| WO | WO99/19724 A1 | 4/1999 | G01N/31/10 |
| WO | WO99/34206 A1 | 7/1999 | G01N/33/10 |
| WO | WO 99/64160 | 12/1999 | B01L/3/02 |
| WO | WO 00/09255 | 2/2000 | B01J/19/00 |

OTHER PUBLICATIONS

M. Dimitrov et al, God. Vissh. Khimikotekhnol. Inst., Sofia 1972, 19, 15–26.*
G. P. Korneichuk et al, Kinet. Katal. 1977, 18, 244–247.*
W. A. Smigiel et al, Ind. Eng. Chem. Fundam. 1979, 18, 419–422.*
P. C. M. van Woerkom et al, Appl. Opt. 1980, 19, 2546–2550.*
M. Steininger et al, J. Chromatog. 1982, 243, 279–284.*
J. G. Creer et al, Appl. Catal. 1986, 22, 85–95.*
U. Rodemerck et al, Microreact. Technol.: Ind. Prospects, Proc. Int. Conf., 3rd 1999, Springer–Verlag: Berlin, Germany, pp. 287–293.*

(List continued on next page.)

Primary Examiner—Arlen Soderquist
(74) Attorney, Agent, or Firm—John G. Tolomei; Frank S. Molinaro; Maryann Maas (57) ABSTRACT

A combinatorial process for simultaneously conducting multiple catalytic chemical reactions in parallel has been developed. At least one catalyst is contained in the reaction zones of a plurality of reactors, each reactor having a reactor insert placed within a sleeve and inserted into a well, the reaction zone of each reactor being formed between a fluid permeable structure attached to the sleeve and a fluid permeable end of the corresponding reactor insert. A fluid reactant is flowed through each reactor where it is contacted with the catalyst contained in the reaction zone to form an effluent. The effluents are removed from the effluent from the reactor and are analyzed.

45 Claims, 5 Drawing Sheets

U.S. PATENT DOCUMENTS

| | | | | |
|---|---|---|---|---|
| 5,612,002 | A | | 3/1997 | Cody et al. .................. 422/131 |
| 5,746,982 | A | | 5/1998 | Saneii et al. ................. 422/134 |
| 5,766,556 | A | | 6/1998 | DeWitt et al. .............. 422/131 |
| 5,785,927 | A | | 7/1998 | Scott et al. .................. 422/104 |
| 5,792,431 | A | | 8/1998 | Moore et al. ................ 422/134 |
| 6,030,917 | A | | 2/2000 | Weinberg et al. ........... 502/104 |
| 6,045,671 | A | | 4/2000 | Wu et al. .............. 204/298.11 |
| 6,056,926 | A | | 5/2000 | Sugarman et al. .......... 422/131 |
| 6,063,633 | A | * | 5/2000 | Willson, III ................. 436/37 |

OTHER PUBLICATIONS

Akporiaye, D. E.; Dahl, I. M.; Karlsson, A.; Wendelbo, R. *Angew Chem. Int. Ed.* 1998, 37, 609–611.

Holzwarth, A.; Schmidt, H.; Maier, W. F. *Angew. Chem. Int. Ed.*, 1998, 37, 2644–2647.

Bein, T. *Angew. Chem. Int. Ed.*, 1999, 38, 323–326.

Senkam, S. M. *Nature*, Jul. 1998, 384(23), 350–353.

Taylor, S. J.; Morken, J. P. *Science*, Apr. 1998, 280(10), 267–270.

Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484–488.

Klien, J.; Lehmann, C. W.; Schmidt, H.; Maier, W. F. *Angew Chem. Int. Ed.* 1998, 37, 3369–3372.

* cited by examiner

COMBINATORIAL PROCESS FOR PERFORMING CATALYTIC CHEMICAL REACTIONS

FIELD OF THE INVENTION

The invention relates to a combinatorial process for performing a plurality of catalytic chemical reactions.

BACKGROUND OF THE INVENTION

Developments in combinatorial chemistry have largely concentrated on the synthesis of chemical compounds. For example, U.S. Pat. Nos. 5,612,002 and 5,766,556 disclose a method and apparatus for multiple simultaneous synthesis of compounds. WO 97/30784-A1 discloses a microreactor for the synthesis of chemical compounds. Akporiaye, D. E.; Dahl, I. M.; Karlsson, A.; Wendelbo, R. *Angew Chem. Int. Ed.* 1998, 37, 609–611 disclose a combinatorial approach to the hydrothermal synthesis of zeolites, see also WO 98/36826. Other examples include U.S. Pat. Nos. 5,609,826, 5,792,431, 5,746,982, and 5,785,927, and WO 96/11878-A1.

More recently, combinatorial chemistry approaches have been applied to catalyst testing to try to expedite the testing process. For example, WO 97/32208-A1 teaches placing different catalysts in a multicell holder. The reaction occurring in each cell of the holder is measured to determine the activity of the catalysts by observing the heat liberated or absorbed by the respective formulation during the course of the reaction, and/or analyzing the products or reactants. Thermal imaging had been used as part of other combinatorial chemistry approaches to catalyst testing; see Holzwarth, A.; Schmodt, H.; Maier, W. F. *Angew. Chem. Int. Ed.*, 1998, 37, 2644–2647, and Bein, T. *Angew. Chem. Int. Ed.*, 1999, 38, 323–326. Thermal imaging may be a tool to learn some semi-quantitative information regarding the activity of the catalyst, but it provides no indication as to the selectivity of the catalyst.

Some attempts to acquire information as to the reaction products in rapid-throughput catalyst testing are described in Senkam, S. M. *Nature* July 1998, 384(23), 350–353 where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. *Angew Chem. Int. Ed.* 1999, 38, 484–488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Combinatorial chemistry has been applied to evaluate the activity of catalysts. Some applications have focused on determining the relative activity of catalysts in a library; see Klien, J.; Lehmann, C. W.; Schmidt, H.; Maier, W. F. *Angew Chem. Int. Ed.* 1998, 37, 3369–3372; Taylor, S. J.; Morken, J. P. *Science*, April 1998, 280(10), 267–270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons which are detected by microelectrode collection. WO 98/07026-A1 discloses miniaturized reactors where the effluent is analyzed during the reaction time using spectroscopic analysis.

Some commercial processes have operated using multiple parallel reactors where the products of all of the reactors are combined into a single product stream; see U.S. Pat. No. 5,304,354 and U.S. Pat. No. 5,489,726.

Applicants have developed a combinatorial process particularly suited for the evaluation of catalysts. Multiple catalytic chemical reactions are conducted in parallel with the resulting reaction mixtures being analyzed. The parallel reactions and the analyses provide a means for the simultaneous evaluation of multiple catalysts or mixtures of catalysts.

SUMMARY OF THE INVENTION

The invention is a combinatorial process for simultaneously conducting multiple catalytic chemical reactions in parallel. The process begins with containing at least one catalyst in the reaction zones of a plurality of reactors, each reactor having a reactor insert placed within a sleeve and inserted into a well, the reaction zone of each reactor being formed between a fluid permeable structure spanning the cross-section of the sleeve and a fluid permeable end of the corresponding reactor insert. A fluid reactant is flowed through a first conduit of each reactor into at least one channel formed by the interior surface of the well and the external surface of the corresponding sleeve into a chamber of each reactor formed by a closed end of the well and the fluid permeable structure attached to the corresponding sleeve. In each reactor, the fluid reactant is flowed from the chamber through the fluid permeable structure spanning the cross-section of the sleeve and into the reaction zone where it is contacted with the catalyst contained in the reaction zone to form an effluent. The effluent is flowed through the fluid permeable portion of the reactor insert and into a second fluid conduit to remove the effluent from the reactor. The effluents from the plurality of reactors are analyzed.

In another specific embodiment of the invention, at least one catalyst is again contained in the reaction zones of a plurality of reactors, where each reactor has a reactor insert placed within a sleeve and inserted into a well, with the reaction zone of each reactor being formed between a fluid permeable structure spanning the cross-section of the sleeve and a fluid permeable end of the corresponding reactor insert. Fluid reactant is flowed through a first conduit of each reactor and through the fluid permeable portion of the reactor insert into the reaction zone of each reactor to contact the catalyst contained in the reaction zone and to form an effluent. The effluent is flowed through the fluid permeable portion structure spanning the cross-section of the sleeve and into at least one channel formed by the interior surface of the well and the external surface of the corresponding sleeve into a second fluid conduit to remove the effluent from the reactor. The effluents from the plurality of reactors are analyzed.

In yet another specific embodiment of the invention, the process begins with providing a plurality of reactors, with the preferred reactor being as follows. Each reactor has a well having an open end and a closed end and a first seal retained by the open end of the well. Each reactor also has a sleeve having a top end and a bottom end. The bottom end of the sleeve is inserted within the open end of the well. A fluid permeable structure is attached to the sleeve and spans the cross-section of the sleeve thereby defining a chamber between the closed end of the well and the fluid permeable structure attached to the sleeve. Each reactor also has a reactor insert having a fluid permeable end and a top end containing a first and a second fluid conduit. The fluid permeable end of the reactor is inserted within the open end of the sleeve. The top end of the reactor insert is engaged with the first seal. The first fluid conduit is in fluid communication with the chamber; and the second fluid conduit is in fluid communication with the bottom end of the reactor insert. A second seal retained by the reactor insert is engaged with the sleeve.

The combinatorial process continues with containing catalyst in each reaction zone; flowing fluid reactant through each first fluid conduit, each chamber, and through each fluid permeable structure attached to the sleeve and into each reaction zone to contact the catalyst therein and form reaction mixtures; flowing the effluents through each fluid permeable end of each reactor insert and removing the effluents through each second fluid conduit; and analyzing the effluents. The flow rate may be controlled so that the catalyst in the reaction zones is in a fluidized bed mode or a fixed bed mode.

In still another specific embodiment of the invention, the plurality of preferred reactors is as described above, but the fluid flow of reactant is reversed. Specifically, the process continues with containing catalyst in the reaction zone; flowing fluid reactant through the second fluid conduit, through the fluid permeable end of the reaction insert and into the reaction zone to contact the catalyst and form an effluent; flowing the effluent through the fluid permeable structure attached to the sleeve, through the chamber and removing the effluent through the first fluid conduit; and analyzing the effluent.

DETAILED DESCRIPTION OF THE INVENTION

In general terms, the invention is a combinatorial process for conducting multiple catalytic chemical reactions in order to evaluate catalysts or mixtures of catalysts. The process begins with providing an array of reactors. Preferably each reactor consists of three main components, (I) a top, or reactor insert, (II) a sleeve, and (III) a bottom, or well. Each of the main components may be constructed out of materials suitable to the application contemplated. The materials chosen are selected to withstand the temperatures, pressures and chemical compounds of the particular application. Examples of suitable materials include metals and their alloys, low grade steel, and stainless steels, super-alloys like incollsy, inconel, hastalloy, engineering plastics and high temperature plastics, ceramics such as silicon carbide and silicon nitride, glass, and quartz. It is not necessary that each component be made of the same material.

The well is preferably cylindrical in shape, but may be of other geometric shapes. For example the cross-section of the well may be in the shape of a square, an ellipse, a rectangle, a polygon, "D"-shaped, segment- or pie-shaped, a chard, or the like. For ease of discussion, the well is discussed here as having a cylindrical shape. The well has a top end, sides, and a bottom end. The top end is open and the bottom end is permanently closed. The preferred volume of the well ranges from about 0.001 $cm^3$ to about 10 $cm^3$ with the two most preferred volumes being 0.1 $cm^3$ and 1 $cm^3$. The preferred size of the well ranges from a length/diameter ratio of about 1 to about 20. It is more preferred that the length/diameter of the wells is greater than 4 and ideally 5 or 10. It is preferred that the well is constructed of material that is able to withstand temperatures of from about 10° C. to about 1000° C. It is also preferred that the well is constructed of material having good heat transfer properties and that the material of construction is inert in the reaction being conducted in the reactor.

The well may be a freestanding unit, or multiple wells may be formed from a single tray or block of material. It is preferred to have a rack or support to which multiple wells are attached. For example, a single support such as a tray, rack, or block of material may support 6, 8, 12, 24, 48, 96, 384, or 1264 wells. It is most preferred that the support unit be similar to the dimensions of a commonly-used microtiter tray. The multiplicity of wells may be heated as a unit, or each well may be individually heated. It is preferred that the open end of the well be flanged. The flange of the open end of the well is used to retain a seal such as an o-ring. The seal engages the reactor insert (discussed in detail below) and operates to form a pressure-tight seal between the well and the reactor insert. Alternate pressure seals may be employed such as VCR, or hoofer fittings, but o-rings are preferred. Optionally, the well may contain a projection extending from the side of the well into the interior of the well to properly position and retain the sleeve (discussed below) within the well. The projection may be located at the closed end of the well at a location where the bottom end of the sleeve (discussed below) rests on the support. The projection may be any of various possibilities such as a shelf, ledge, or lip. It is more preferred however, that the sleeve be self-supporting with the well as discussed below.

In the preferred embodiment, a reactor insert is inserted into a sleeve which in turn is inserted into the well. In the assembled reactor, the sleeve is positioned between the reactor insert and the well. As with the well, the sleeve is preferably cylindrical in shape, but may be of other geometric shapes. For example, the general cross-section of the sleeve may be in the shape of a square, an ellipse, a rectangle, a polygon, "D"-shaped, segment- or pie-shaped, cog- or gear-shaped, a chard, or the like. It is preferred that the geometry of the sleeve be chosen to coordinate with the geometry of the well. It is most preferred that the sleeve is cylindrical and, for ease of discussion, the sleeve is discussed here as having an overall cylindrical shape.

The sleeve has a top end, sides, and a bottom end. The top and bottom ends of the sleeve are open. A microporous containment device, which may be constructed of any material that is capable of retaining solid particles while allowing gas or liquid to pass through, is attached at or near the bottom end of the sleeve and extends across the cross-section, or internal diameter, of the sleeve. Examples include frits, membranes, or fine meshed screens. Suitable frits include sintered metal, glass, sintered glass, and raney metals. Suitable membranes include electro-bonded films and etched alloy films. Frits are preferred for the microporous containment device at or near the bottom of the sleeve, and it is preferred that the frit cover as much of the cross-section of sleeve as possible, and most preferred that the frit cover as close to 100 percent of the cross section of the sleeve as practical. It is most preferred to have a frit with small passages so that the fluid is well dispersed after passing through the frit. The interior volume of space defined by the top of the sleeve, sides of the sleeve, and the microporous containment device attached to the sleeve is a reaction zone and contains solid catalyst particles.

The external diameter of the sleeve is less than the internal diameter of the well so that the sleeve may be inserted into the well. In one embodiment of the invention, the length of the sleeve may be less than the length of the well so that a chamber is formed between the bottom end of the sleeve and the bottom end of the well. It is preferred that the length of the sleeve be from about 70% to about 95% of the length of the well. In another more preferred embodiment of the invention, the sleeve extends the entire length of the well so that the bottom end of the sleeve is resting on the bottom of the well. In this embodiment, the microporous containment device is located near but not at the bottom end of the sleeve. Furthermore, in this embodiment, the sides of the sleeve at the bottom end of the sleeve have portions removed so that as the bottom end of the sleeve rests on the bottom end of well, channels are formed through which fluid is able to flow. For example, the bottom end of the sleeve may have ridges, or be scalloped or grooved.

It is preferred that the sleeve is constructed of material that is able to withstand temperatures of from about 10° C. to about 1000° C. and it is preferred that the sleeve be constructed of material as was used for the well. It is also preferred that the sleeve be constructed of material having good heat transfer properties.

The sleeve and the well are sized so that with the sleeve inserted into the well, the external surface of the sleeve and the internal surface of the well form channels through which a fluid is able to flow. It is preferred that either the external surface of the sleeve or the internal surface of the well, or both, define grooves that upon insertion of the sleeve into the well form the channels. The grooves may run parallel to the length of the sleeve, may follow the circumference of the sleeve in a spiral pattern, or may form a wave pattern. The channels formed by the grooves provide a path for fluid to flow from one end of the sleeve to the other. For example, the fluid may flow from the top of the sleeve to the chamber formed between the fluid permeable structure attached to the sleeve and the bottom of the well. From this chamber, the fluid may pass through the fluid permeable structure attached to the sleeve and into the reaction zone containing the solid catalyst particles.

The sleeve is preferably sized, and the grooves formed, so that a portion of the external surface of the sleeve remains in contact with the internal surface of the well. Such contact provides for good heat transfer from the well to the sleeve. Many reactions require heat, and good heat transfer from the well to the sleeve provides a mode for heating the reaction zone defined by the sleeve and the catalyst within the reaction zone. It is generally desirable to preheat the reactant prior to introduction to the reaction zone, and good heat transfer between the well and the sleeve provides for an opportunity to preheat the reactant as it passes with the fluid flow through the channels. The pattern chosen for the grooves may vary depending upon the degree of preheating needed for the reactant and the particular reaction involved. For example, grooves and therefore channels that run parallel to the length of the sleeve would provide less residence time of the fluid within the channels and less preheating. On the other hand, grooves and channels that spiral around the circumference of the sleeve provide greater residence time of the fluid within the channels and greater preheating, but may allow time for background reactions to occur.

A reactor insert is inserted into the sleeve. The reactor insert has a top end, sides, and a bottom end containing a fluid permeable portion. As with the well and the sleeve, the reactor insert is preferably cylindrical in shape, but may be of other geometric shapes such as a cross-section in the shape of a square, an ellipse, a rectangle, a polygon, "D"-shaped, segment- or pie-shaped, cog- or gear-shaped, a chard, or the like. However, with the reactor insert, it is preferable to have the geometry of the reactor insert conform to the geometry of the interior of the sleeve. For ease of discussion, the reactor insert is discussed here as having a cylindrical shape. The top end provides a fluid conduit and the bottom end contains a fluid permeable portion. It is preferred that the reactor insert be constructed of material that is able to withstand temperatures of from about 10° C. to about 1000° C. and it is preferred to construct the reactor insert from the same material as the well and the sleeve.

The external diameter of the reactor insert is less than the internal diameter of the sleeve so that the reactor insert may be inserted into the sleeve. The length of the reactor insert is less than the length of the sleeve between the top end and the fluid permeable structure so that a reaction zone is formed between the bottom end of the reactor insert and the fluid permeable structure attached to the sleeve. Solid catalyst particles are retained within the reaction zone. It is preferred that the length of the reactor insert be from about 5% to about 70% of the length of the sleeve measured from the top end to the fluid permeable structure attached to the sleeve.

As stated above, the bottom end of the reactor insert contains at least a portion that is permeable to fluid. The portion permeable to fluid may be any material that is capable of excluding solid particles while allowing gas or liquid to pass through. Examples include frits or membranes as discussed above for the sleeve. Frits are preferred for the permeable portion of the bottom of the reactor insert, and it is preferred that the frit cover a substantial portion of the bottom of the reactor insert, greater than 90% is preferred. The interior of the reactor insert forms a passage to allow fluid to flow from one end of the reactor insert to the other. For example, the fluid that permeates through the permeable portion of the bottom end of the reactor insert may pass to the top end of the reactor insert and exit the reactor via the fluid conduit at the top end of the reactor insert. Catalyst particles are unable to pass through the permeable portion of the bottom end of the reactor insert and are therefore retained within the reaction zone.

It is preferred that the top end of the reactor insert be flanged. The flanged portion of the reactor insert would engage the o-ring seal retained by the flange of the well to form a pressure-tight seal between the reactor insert and the well via the o-ring. The reactor insert is further equipped with a seal to engage the sleeve and form a pressure-tight seal between the reactor insert and the sleeve. Optionally, the reactor insert may be equipped with a thermocouple. The thermocouple may extend from the top of the reactor insert, through the interior passage of the reactor insert, and through the bottom of the reactor insert to extend into the reaction zone. The thermocouple provides accurate measurements of the temperature at which a reaction in the reaction zone is occurring. It is preferred that the thermocouple be housed within a guide tube that also extends from the top of the reactor insert, through the interior passage of the reactor insert, and through the bottom of the reactor insert into the reaction zone. The guide tube, which is open at both a top end and a bottom end, allows for easy insertion or removal of the thermocouple.

As discussed above, one fluid conduit is located at the top end of the reactor insert. A second fluid conduit may be positioned in a variety of locations to allow fluid to pass to or exit from the channels formed by the sleeve and the well. A preferred location for the second fluid conduit is for the conduit to pass through the flange of the reactor insert and conduct fluid into a volume of space between the flange of the reactor insert and the flange of the well. The volume of space is further defined by the o-ring seal retained by the flange of the well and the side of the reactor insert. Alternatively, the second fluid conduit may pass through the side of the well and provide a passage for fluid to flow into or out of the channels formed by the sleeve and the well. It is preferred that the second fluid conduit pass through the flange of the reactor insert to the volume of space between the flange of the reactor insert and the flange of the well so that all fluid conduits are a part of the reactor insert. In a specific embodiment of the invention either the first or the second fluid conduit is in fluid communication with a reactant reservoir. Similarly, the fluid conduit that is not in fluid communication with a reactant reservoir may be in fluid communication with a sampling device that is used to sample the effluent fluid exiting the reactor.

In combinatorial chemistry applications, an array of reactors are used in parallel to conduct multiple reactions simultaneously. The preferred reactor described above is successfully used in combinatorial chemistry applications. It is preferred that the multiple wells of a number of reactors are attached to a single support such as a rack or tray (described above). The multiple reactor inserts are also preferably attached to a single support such as a top plate. For combinatorial chemistry applications, a single top plate is engaged with a single rack containing multiple wells to form a multiple of individual reactors. However, it is preferred to have the sleeves be individually movable. The reactor sleeves may be used in the synthesis of different catalysts, and the sleeves, still containing the catalysts, are inserted into the wells as described above. The advantage would be the elimination of a catalyst transfer step since the catalyst would remain in the sleeve from the time of synthesis through the testing process. It is preferred that the same reactant reservoir be in fluid communication with each of the multiple reactors.

The combinatorial process of the present invention makes use of the above-described array of reactors to simultaneously conduct multiple catalytic chemical reactions. The process begins with charging catalyst to each reaction zone. As discussed above, the sleeves of the reactors may have been used in the synthesis of new catalysts and therefore may contain solid catalyst particles. Alternatively, solid catalyst particles may be loaded into the sleeves and the reactors assembled.

Fluid reactant, or a fluid stream containing fluid reactant, is then introduced simultaneously to the array of reactors. It is preferred that a single reactant reservoir be used as the source of fluid reactant for all of the reactors in the array. For ease of explanation, the process is described in detail with reference to a single reactor in the array, however, in actual practice, each act is performed simultaneously in all reactors in the array. The fluid reactant enters each reactor through the corresponding first fluid conduit and then passes through one or more channels between the sleeve and the well to enter the chamber formed between the closed end of the well and the fluid permeable structure attached to the sleeve. The fluid reactant then passes through the fluid permeable structure and into the reaction zone to contact the catalyst contained therein to form an effluent. Upon contacting the catalyst, a reaction may be catalyzed and product compounds may be formed. However, since the process of the invention may be used to evaluate the performance of catalysts including testing catalysts of unknown capacity to catalyze a given reaction, it is expected that in some circumstances no reaction would be catalyzed. The effluents may therefore contain only fluid reactant or a mixture of fluid reactant and products with the mole ratio of fluid reactant to products varying from about 1:1000 to about 1000:1. It is also possible that the effluent would contain only reaction products.

The effluent passes through the fluid permeable end of the reactor insert and is removed from each reactor via the second fluid conduits. The effluent is then analyzed using an analytical technique to determine whether products have been formed, how much product has been formed, and/or which specific product compounds have been formed. The analytical technique used may be any suitable technique for the type of information desired and components involved. Preferred techniques include chromatography techniques, spectroscopy techniques, nuclear magnetic resonance techniques and combinations thereof. At least a portion of the effluent is removed from each reactor and is conducted to the analytical instrument, and the identity and amount of the components in the effluent is determined.

The specific analysis performed depends upon the application and the desired information. For example, if only the activity of the plurality of catalysts are to be determined and compared, an analysis measuring the amount of reactant consumed in each reaction mixture may be sufficient. Also, a qualitative analysis for the composition of the effluent could be used as an indication of catalyst activity. However, it is generally preferred to have both activity information as well as selectivity and yield information and, in that case, the analytical technique would be selected to measure the quantity of the different components present in each reaction mixture. Using both the activity information and the selectivity information, the yield could be calculated. Any or all of the variables may be compared between the individual catalysts or mixtures of catalysts that form the plurality of catalysts, and the catalysts may be evaluated.

The effluent from each reactor may be analyzed continuously as it exits the reactor, flowed directly to analytical instrumentation, or may be sampled prior to analysis. When the sampling option is selected, it is preferred that the sampling of the effluent from each reaction is conducted simultaneously. The benefit of simultaneous sampling is that the results from each catalyst bed are more readily comparable since each catalyst bed would be exposed to reactant for the same period of time. This is perhaps best described using an example. In a 48 reactor array, if the sampling of the 48 reaction mixtures were to occur sequentially, and the time needed for each sampling was one minute, there would be a 48 minute time difference between the first reactor being sampled and the last reactor being sampled. Therefore, the overall time the last catalyst would be exposed to the reactant would be 48 minutes longer than the overall time the first catalyst would be exposed to the reactant. It is known that the activity and selectivity of catalysts may change over the time the catalyst is in use. During the 48 minutes between the sampling of the first and last reactor, the activity and selectivity of the catalyst in the last reaction may have significantly changed. Sequential sampling has the likelihood of introducing error since the time the catalyst is in use would become a variable as opposed to being identical for all reactors.

In evaluating catalyst performance, observing trends of activity, selectivity, and yield over time is valuable. Therefore, in a specific embodiment of the present invention as the reactant is continuously introduced to each catalyst bed and reaction mixture is continuously withdrawn from each reactor, each of the effluents is periodically sampled and analyzed as discussed above. The activity, selectivity and/or yield are determined at each sampling and analysis interval, and the trend of the activity, selectivity and/or yield may be observed over time. Again it is preferred that the effluents of each of the reactors is sampled simultaneously so that the analysis results are directly comparable and the time that each catalyst has been exposed to reactant is the same.

The superficial or linear velocity of the fluid reactant may be controlled so that the catalyst(s) in the reaction zones are either in a fixed bed or in a fluidized bed, and in a single catalyst evaluation the superficial or linear velocity of the fluid reactant may be varied to evaluate the catalyst in both a fluidized bed and a fixed bed. The superficial velocity is the amount of gas fed per unit of time and unit of reactor cross-sectional area. If the superficial velocity of the fluid reactant is low enough, the gravimetric force operating on the catalyst particles will be greater than the lifting or frictional force provided by the fluid reactant, and the catalyst will remain in a fixed bed resting on the fluid permeable structure attached to the sleeve. If the superficial velocity is high enough, the frictional force provided by the fluid reactant will completely overcome the gravimetric force operating on the catalyst particles, and the catalyst particles will be forced against the fluid permeable end of the reactor insert and held in a fixed bed. However, the superficial velocity of the reactant fluid may be adjusted so that the catalyst bed is fluidized. Furthermore, an inert fluid may be used to fluidize the beds. The reactant may be mixed with the inert fluid, or may be introduced independently or intermittently. Equations to calculate the superficial velocity needed to fluidize a catalyst bed are known, $$U_{mf} = 1.118 \times 10^{-13} \times \frac{d_{p,sv}^{1.82}}{\rho_g^{0.06}} \frac{(\rho_s - \rho_g)^{0.94}}{\mu^{0.88}}$$

$$\frac{U_{mf}}{U_{mb}} = \frac{2363 \times \rho_g^{0.126} \mu^{0.523} \exp(0.716F)}{d_{p,sv}^{0.8}(g^{0.934}(\rho_s - \rho_g))^{0.934}}$$

Where:
  $U_{mf}$=minimum fluidization velocity
  $U_{mb}$=minimum bubbling velocity
  $d_{p,sv}$=mean diameter of particles
  $\rho_g$=gas density
  $\mu$=viscosity
  $\rho_s$=solid particle density
  F=fraction of particles below 40 microns
  g=gravitational constant In an application where the particle size of the catalyst is known or is measured, one of ordinary skill in the art would understand how to solve the above equations to determine the proper superficial velocity for the fluid reactant in order to fluidize the catalyst bed in the reaction zone. However, in an application where the particle size of the catalyst is not known, the standard equations above could not be solved.

Figure 7:
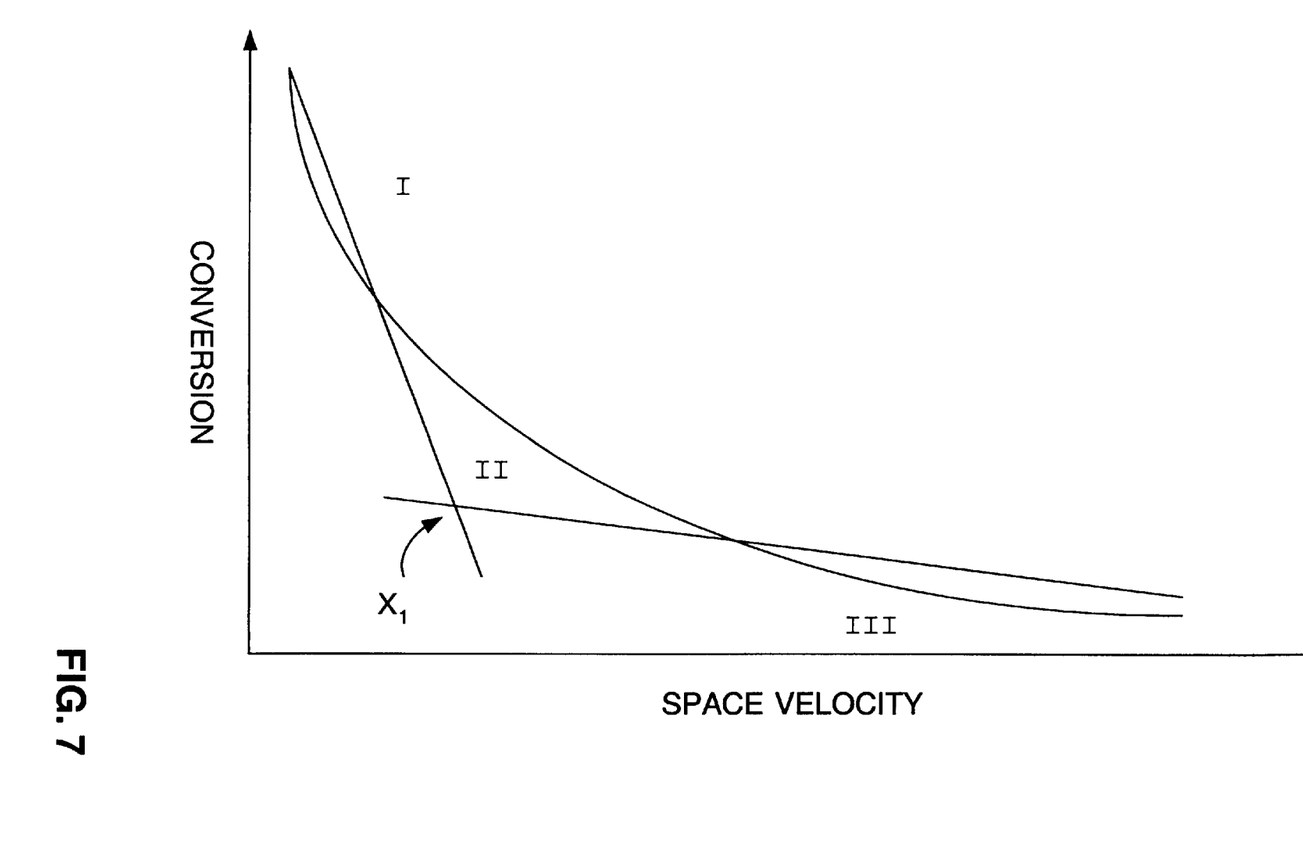
FIG. 7 is a sample plot of superficial velocity versus conversion.

Applicants have discovered a procedure to determine the superficial velocity needed to fluidize a solid particle catalyst bed when the particle size and density of the catalyst particles are not known. The process involves ramping the superficial velocity while monitoring the conversion provided by the catalyst. All other operating conditions remain constant. FIG. 7 presents a sample graph of velocity versus conversion and shows that the curve can be divided into three regions. In Region I, the highest conversion is at the lowest superficial velocity and the conversion decreases exponentially as the superficial velocity is increased. As the superficial velocity is increased further, the slope of the curve markedly changes, i.e., becomes less negative until a plateau-like area is reached. The superficial velocity between where the slope changes substantially and where plateauing is observed is the range of superficial velocities which results in fluidization of the catalyst and is labeled Region II. As the superficial velocity becomes too great for fluidization, a fixed bed regime will again occur through pinning of the catalyst against the upper frit and the conversion is expected to decline (approaches zero) with increasing superficial velocity. This is Region III.

The curve in Region I can be approximated with a straight line (line 1) and is extended to the x-axis. The curve in Region III can also be approximated by a straight line (line 2) and extended until it meets the y-axis. The intersection of these two lines is a point having a superficial velocity ($x_1$) to whose immediate right, i.e., greater superficial velocity defines Region II where fluidization occurs.

Thus, monitoring the conversion as the superficial velocity is increased followed by a graphical analysis of the data is a method to determine the range of superficial velocities that will result in a fluidized catalyst bed. This method is preferably used in the case where the particle size of the catalyst is not known and standard equations are not sufficient. To aid in achieving proper fluidization, it is preferred that the path of fluid reactant just prior to passing through the fluid permeable structure attached to the sleeve be perpendicular to the fluid permeable structure attached to the sleeve.

In another embodiment of the invention, the fluid reactant is flowed through the reactors in a direction that is the reverse of that described above. Fluid reactant is flows through a first conduit of each reactor that is in fluid communication with the reactor insert and through the fluid permeable portion of the reactor insert into the reaction zone of each reactor. In each reactor, the fluid reactant contacts the catalyst contained in the reaction zone to form an effluent. The effluent flows through the fluid permeable structure attached to the sleeve and into at least one channel formed by the interior surface of the well and the external surface of the corresponding sleeve into a second fluid conduit to remove the effluents from the reactor; and the effluents are analyzed. The analyzing, sampling, monitoring over time, and controlling superficial velocity options discussed previously also apply in this specific embodiment.

In some catalyst evaluations, it is advantageous to compare catalyst performance in a fixed bed with the catalyst performance in a fluidized bed. Therefore, in a catalyst evaluation it may be desirable to flow the fluid in one direction to achieve a fluidized bed, and then flow the fluid in the reverse direction to achieve a fixed bed with the fluid remaining at the same superficial velocity. The order may be changed to run the fixed bed first and the fluidized bed second. In more specific terms, the reactors are as described above with a well having an open end and a closed end; a first seal retained by the flanged open end of the well; a sleeve having a top end, a bottom end, and a cross section, the bottom end inserted within the open end of the well; a fluid permeable structure attached to the sleeve and spanning at least a portion of the cross section of the sleeve and defining a chamber between the closed end of the well and the fluid permeable structure attached to the sleeve; a reactor insert having a fluid permeable end and a top end containing a first and a second fluid conduit, the fluid permeable end inserted within the top end of said sleeve forming a reaction zone between the fluid permeable structure attached to the sleeve and the fluid permeable end of the reactor insert, the top end of the reactor insert engaged with the first seal, the first fluid conduit in fluid communication with said chamber; the second fluid conduit in fluid communication with the fluid permeable end of the reactor insert; and a second seal retained by the reactor insert and engaged with the sleeve. Catalyst is charged to the reaction zones. Fluid reactant is flowed through the first fluid conduits, the chambers, and through the fluid permeable structures attached to the sleeves and into the reaction zones at superficial velocity sufficient to maintain the catalyst in the reaction zones in a fluidized bed mode, to contact the catalyst therein and form reaction mixtures. The resulting effluents are flowed through the fluid permeable ends of the reactor inserts and removed through the second fluid conduits and analyzed. Fluid flow is then switched, preferably using valves, so that fluid reactant is now flowed through the second fluid conduits, through the fluid permeable end of the reaction inserts and into the reaction zones at the same superficial velocity as above to contact the catalyst and form reaction mixtures. The resulting effluents are flowed through the fluid permeable structures attached to the sleeves, through the chambers, removed through the first fluid conduits and analyzed. The sequence of the direction fluid flow may be in any order.

Figure 1:
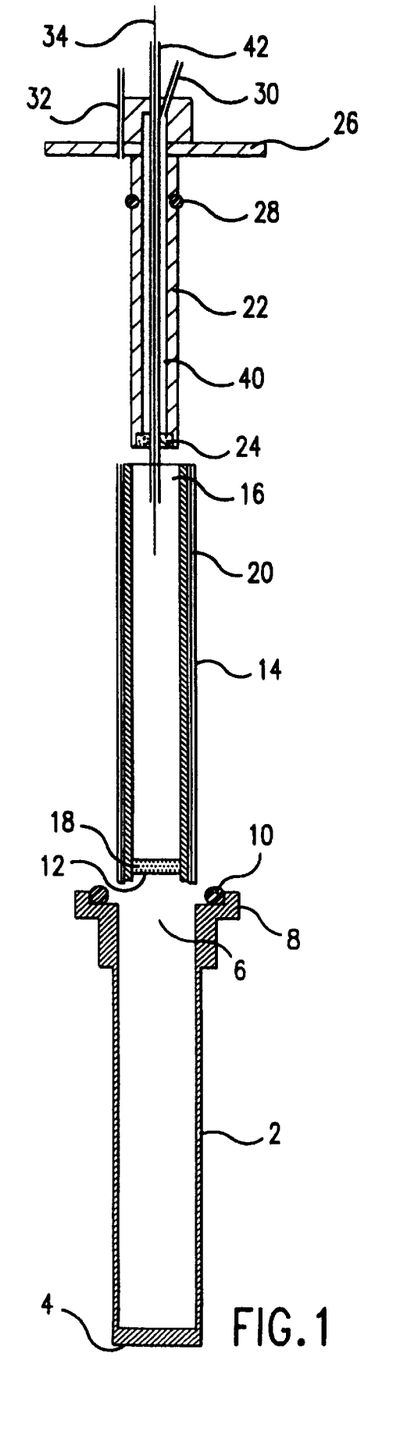
FIG. 1 is an exploded side view of a preferred reactor.
Figure 2:
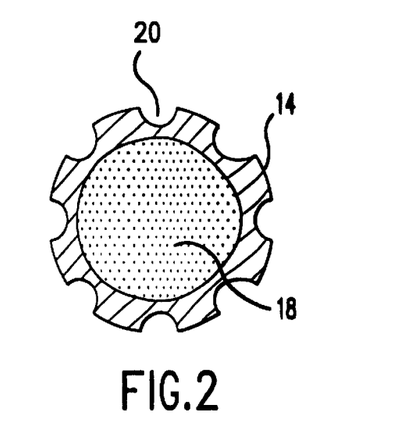
FIG. 2 is an end view of the sleeve of the preferred reactor.
Figure 3:
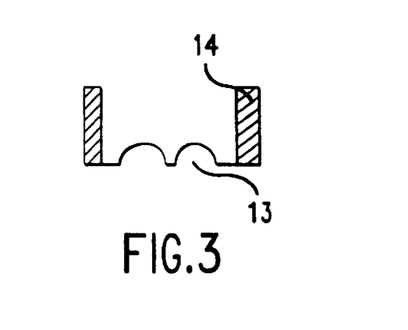
FIG. 3 is an enlarged view of the bottom end of the sleeve.
Figure 4:
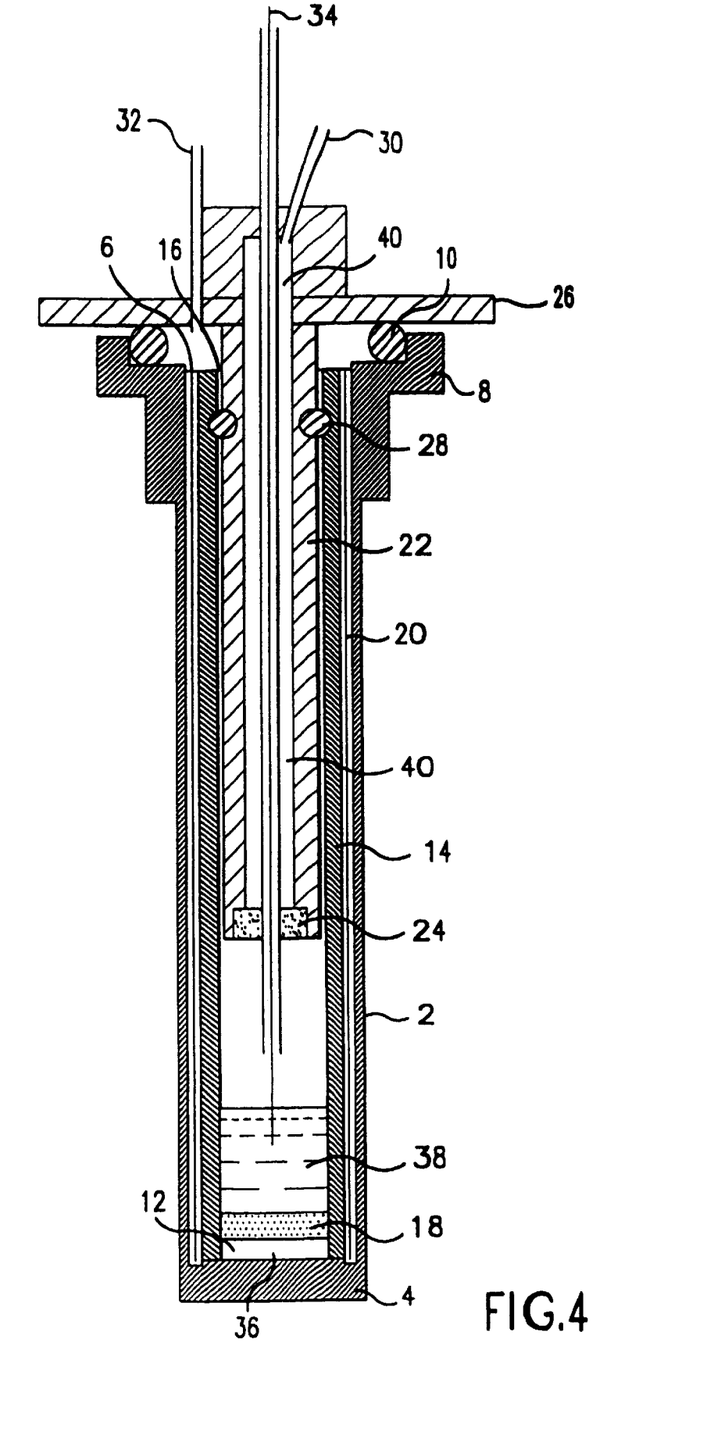
FIG. 4 is an assembled side view of the preferred reactor.

Referring to FIG. 1, an exploded side view of the reactor of the invention, well 2, has a closed end 4 and an open end 6. Open end 6 contains a flange 8 which retains o-ring 10. Sleeve 14 has open end 16 and bottom end 12. Near bottom end 12 is frit 18. The walls of sleeve 14 have material removed to form grooves 20 as shown in FIG. 2, an end view of sleeve 14. The bottom end 12 of sleeve 14 has material removed to form ridges 13, as shown in FIG. 3, and external side view of bottom end 12 of sleeve 14. Reactor insert 22 has fluid permeable end 24 in fluid communication with fluid conduit 30 via hollow center 40. Reactor insert 22 has flanged end 26, fluid conduit 32, and o-ring 28. Thermocouple 34 extends through guide tube 42 which in turn extends through reactor insert 22 and beyond fluid permeable end 24 of reactor insert 22. Referring to FIG. 4, bottom end 12 of sleeve 14 is inserted into open end 6 of well 2 with the bottom end 12 of sleeve 14 resting on the closed end 4 of well 2. Fluid permeable end 24 of reactor insert 22 is inserted into open end 16 of sleeve 14. A reaction zone 38 is formed between the fluid permeable end 24 of reactor insert 22 and the frit 18 of sleeve 14. Catalyst is retained in reaction zone 38. Chamber 36 is formed by closed end 4 of well 2 and frit 18 of sleeve 14. Flange end 26 of reactor insert 22 engages o-ring 10 retained by flange 8 of well 2 to form a pressure tight seal. o-ring 28 of reactor insert 22 engages sleeve 14 to form a pressure tight seal.

Fluid enters the reactor via conduit 32. Grooves 20 of sleeve 14 together with well 2 form passages allowing fluid from conduit 32 to flow through grooves 20 and grooves 13 to chamber 36 formed by closed end 4 of well 2 and frit 18 of sleeve 14. Fluid passes through fluid permeable frit 18 of sleeve 14 and enters reaction zone 38 to contact the catalyst. The fluid flow may be at a rate to result in a fluidized bed of catalyst or fixed bed of catalyst, whichever is required for the specific application. Thermocouple 34 is used to accurately measure the temperature of reaction zone 38. After contacting the catalyst in reaction zone 38, the fluid passes through fluid permeable end 24 of reactor insert 22, through hollow center 40, and is removed from the reactor via fluid conduit 30.

Alternatively, fluid may be introduced to the reactor via fluid conduit 30. The fluid passes through hollow center 40 of reactor insert 22 and through fluid permeable end 24 of reactor insert 22 into reaction zone 38. With the fluid flowing in this direction, it is preferred that the flow rate be such that the catalyst remains as a fixed bed. After contacting the catalyst in reaction zone 38, the fluid passes through frit 18 of sleeve 14 and into chamber 36. The fluid then flows through passages formed by grooves 20 and 13 of sleeve 14 together with well 2 to the open flanged end 6 of well 2. The fluid exits the reactor via fluid conduit 32.

Figure 5:
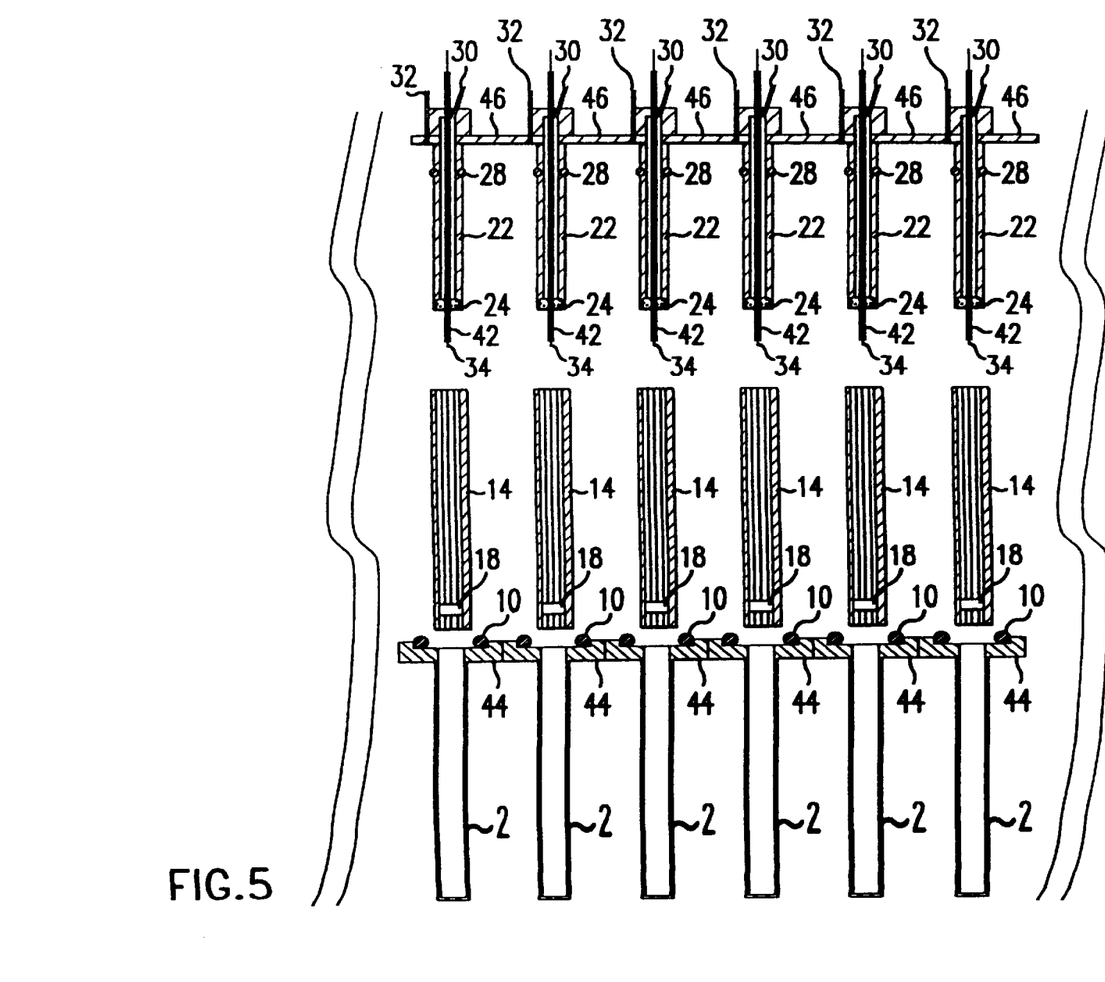
FIG. 5 is an exploded side view of a plurality of preferred reactors.

FIG. 5 is an exploded side view of an array of reactors having wells 2, sleeves 14 and reactor inserts 22. The wells 2 are as described above including retaining o-rings 10. However, the multiple wells 2 are attached to a support 44. The sleeves 14 are as described above, including the attachment of frits 18. Reactor inserts 22 are as described above including having fluid permeable ends 24 in fluid communication with fluid conduits 30, thermocouples 34 extending through guide tubes 42, fluid conduits 32, and o-rings 28. Reactor inserts 22 are attached to a top plate 46.

Figure 6:
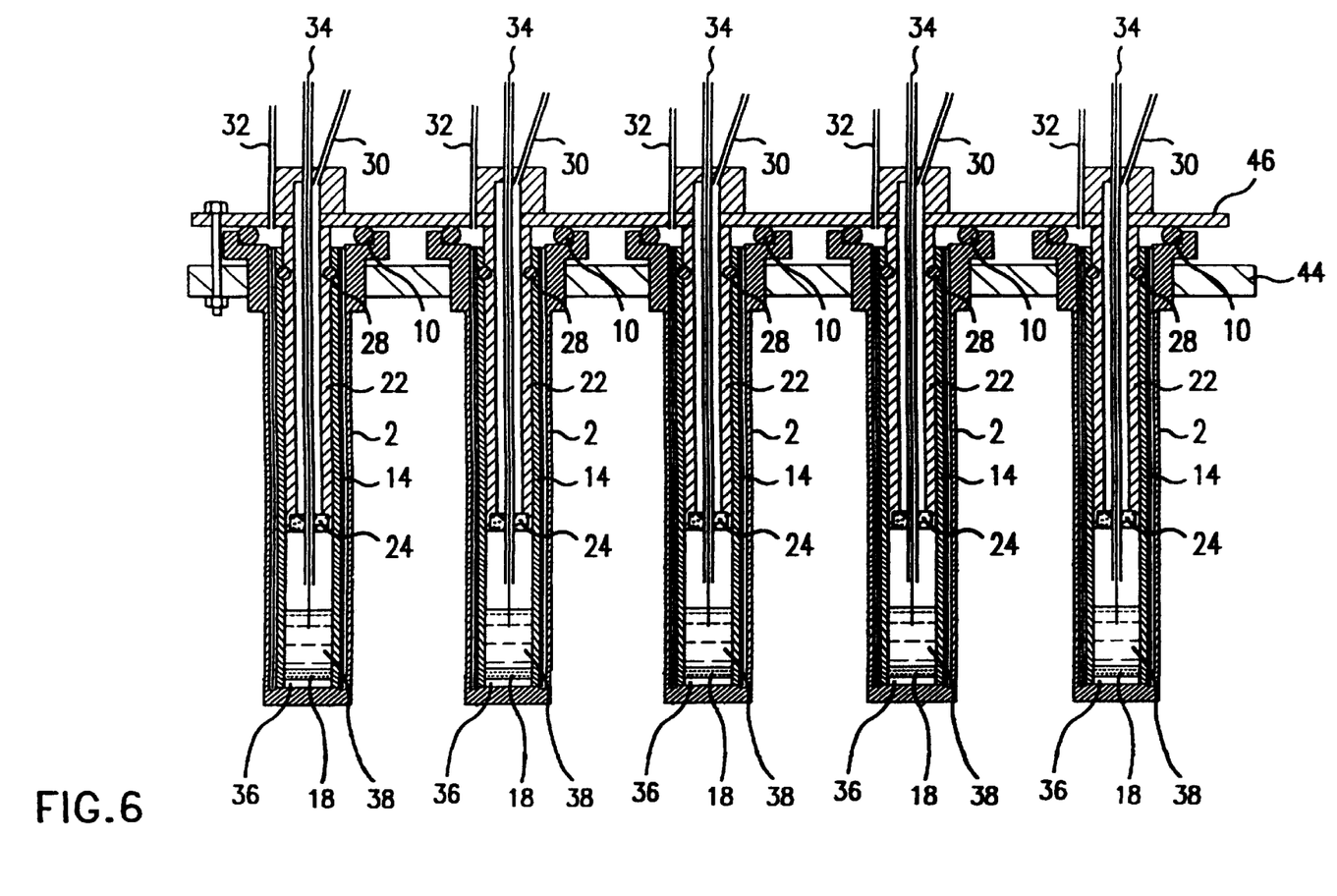
FIG. 6 is an assembled side view of a plurality of preferred reactors.

Referring to FIG. 6, sleeves 14 are inserted into wells 2. Fluid permeable ends 24 of reactor inserts 22 are inserted into sleeves 14. Reaction zones 38 are formed between the fluid permeable ends 24 of reactor inserts 22 and the frits 18 of sleeves 14. Catalyst is retained in reaction zones 38. Chambers 36 are formed by wells 2 and frits 18 of sleeves 14. Reactor inserts 22 engage o-rings 10 retained by wells 2 to form a pressure tight seal. O-rings 28 of reactor inserts 22 engage sleeves 14 to form a pressure tight seal.

The plurality of the reactors described above are used simultaneously in the process of the present invention. In one specific embodiment of the invention, fluid reactant enters each reactor in the plurality of reactors via conduit 32. Grooves 20 of sleeve 14 together with well 2 form passages allowing fluid from conduit 32 to flow from open end 16 of sleeve 14 through grooves 20 to chamber 36 formed by closed end 4 of well 2 and fluid permeable structure 18 attached to sleeve 14. Fluid passes through fluid permeable structure 18 attached to sleeve 14 and enters reaction zone 38. The superficial velocity of the fluid reactant may be of a rate to result in a fluidized bed of catalyst or fixed bed of catalyst, whichever is required for the specific application. Thermocouple 34 in guide tube 42 is used to accurately measure the temperature of reaction zone 38. The fluid reactant contacts the catalyst in reaction zone 38 and a fluid reaction mixture is formed. The fluid reaction mixture passes through fluid permeable end 24 of reactor insert 22, through hollow center 40, is removed from the reactor via fluid conduit 30, and is analyzed using an analytical technique specific to the nature of the compounds involved.

Alternatively, fluid reactant may be introduced to the reactor via fluid conduit 30. The fluid reactant passes through hollow center 40 of reactor insert 22 and through fluid permeable end 24 of reactor insert 22 into reaction zone 38. With the fluid reactant flowing in this direction, it is preferred that the flow rate be such that the catalyst remains as a fixed bed. The fluid reactant contacts the catalyst in reaction zone 38, forming an effluent. The effluent passes through fluid permeable structure 18 attached to sleeve 14 and into chamber 36. The effluent then flows through passages formed by grooves 13 of sleeve 14 and grooves 20 of sleeve 14 together with well 2 to the open flanged end 6 of well 2. The effluent exits the reactor via fluid conduit 32 and is analyzed using an analytical technique specific to the nature of the compounds involved.

What is claimed is:

1. A process for evaluating the performance of multiple catalysts comprising:
   a) containing at least one catalyst in the reaction zones of a plurality of reactors, each reactor having a reactor insert placed within a sleeve and inserted into a well, said sleeve having a cross-section spanned by an attached fluid permeable structure, the reaction zone of each reactor being formed between the fluid permeable structure attached to the sleeve and a fluid permeable end of the corresponding reactor insert;
   b) flowing fluid reactant through a first conduit of each reactor into at least one channel formed by the interior surface of the well and the external surface of the corresponding sleeve into a chamber of each reactor formed by a closed end of the well and the fluid permeable structure attached to the corresponding sleeve;
   c) flowing, in each reactor, the fluid reactant from the chamber through the fluid permeable structure attached to the sleeve and into the reaction zone;
   d) contacting, in each reactor, the fluid reactant with the catalyst contained in the reaction zone to form an effluent;
   e) flowing, in each reactor, the effluent through the fluid permeable portion of the reactor insert and into a second fluid conduit to remove the effluent from the reactor; and
   f) analyzing the effluents.

2. The process of claim 1 wherein the fluid reactant is flowing through the first fluid conduits at a superficial velocity sufficient to fluidize the catalyst in the reaction zones.

3. The process of claim 2 further comprising determining the superficial velocity sufficient to fluidize the catalyst in the reaction zones by ramping the superficial velocity of the of the fluid reactant flowing through the first fluid conduits while monitoring the conversions achieved by the catalysts in the reaction zones; plotting the superficial velocity versus conversion and graphically analyzing the plot in order to define a range of superficial velocities which fluidize the catalysts.

4. The process of claim 1 wherein the fluid reactant flowing through the first fluid conduits is at a superficial velocity sufficient to maintain the catalyst in the reaction zones in a fixed bed for a period of time and at a superficial velocity sufficient to maintain the catalyst in the reaction zones in a fluidized bed for a period of time.

5. The process of claim 1 wherein the fluid reactant is flowing through the first fluid conduits at a superficial velocity sufficient to maintain the catalyst in the reaction zones in a fixed bed.

6. The process of claim 1 further comprising an inert fluid flowing through the first fluid conduits at a superficial velocity sufficient to fluidize the catalyst in the reaction zones.

7. The process of claim 1 further comprising analyzing the effluents periodically over time.

8. The process of claim 1 further comprising sampling the effluents prior to analyzing the effluents.

9. The process of claim 1 further comprising simultaneously sampling the effluents prior to analyzing the effluents.

10. The process of claim 1 wherein the effluents are analyzed by an analytical technique selected from the group consisting of chromatography, spectroscopy, nuclear magnetic resonance, and combinations thereof.

11. The process of claim 1 further comprising preheating the fluid reactant prior to passing through the fluid permeable structures attached to the sleeves and into the reaction zones.

12. The process of claim 1 further comprising measuring the temperature in the reaction zones.

13. The process of claim 1 further comprising calculating from the results of the analysis of the effluent a variable selected from the group consisting of activity, selectivity, yield, or a combination thereof.

14. The process of claim 13 further comprising comparing the catalysts contained in the plurality of reactors on the basis of the activity, selectivity, yield, or a combination thereof.

15. A process for evaluating the performance of multiple catalysts comprising:
   a) containing at least one catalyst in the reaction zones of a plurality of reactors, each reactor having a reactor insert placed within a sleeve and inserted into a well, said sleeve having a cross-section spanned by an attached fluid permeable structure, the reaction zone of each reactor being formed between the fluid permeable structure attached to the sleeve and a fluid permeable end of the corresponding reactor insert;
   b) flowing fluid reactant through a first conduit of each reactor and through the fluid permeable portion of the reactor insert into the reaction zone of each reactor;
   c) contacting, in each reactor, the fluid reactant with the catalyst contained in the reaction zone to form an effluent;
   d) flowing, in each reactor, the effluent through the fluid permeable structure attached to the sleeve and into at least one channel formed by the interior surface of the well and the external surface of the corresponding sleeve into a second fluid conduit to remove the effluents from the reactor; and
   e) analyzing the effluents.

16. The process of claim 15 further comprising analyzing the effluents periodically over time.

17. The process of claim 15 further comprising sampling the effluents prior to analyzing the effluents.

18. The process of claim 15 further comprising simultaneously sampling the effluents prior to analyzing the effluents.

19. The process of claim 15 wherein the effluents are analyzed by an analytical technique selected from the group consisting of chromatography, spectroscopy, nuclear magnetic resonance, and combinations thereof.

20. The process of claim 15 further comprising measuring the temperature in the reaction zones.

21. The process of claim 15 further comprising calculating from the results of the analysis of the effluent a variable selected from the group consisting of activity, selectivity, yield, or a combination thereof.

22. The process of claim 21 further comprising comparing the catalysts contained in the plurality of reactors on the basis of the activity, selectivity, yield, or a combination thereof.

23. A process for evaluating the performance of multiple catalysts comprising a) providing a plurality of reactors each comprising:
  i) a well having an open end and a closed end;
  ii) a first seal retained by said flanged open end of said well;
  iii) a sleeve having a top end, a bottom end, and a cross section, said bottom end inserted within said open end of the well;
  iv) a fluid permeable structure attached to said sleeve and spanning at least a portion of the cross section of the sleeve and defining a chamber between said closed end of the well and said fluid permeable structure attached to said sleeve;
  v) a reactor insert having a fluid permeable end and a top end containing a first and a second fluid conduit, said fluid permeable end inserted within said top end of said sleeve forming a reaction zone between said fluid permeable structure attached to said sleeve and said fluid permeable end of said reactor insert, said top end of the reactor insert engaged with said first seal, said first fluid conduit in fluid communication with said chamber; said second fluid conduit in fluid communication with said fluid permeable end of said reactor insert; and
  vi) a second seal retained by said reactor insert and engaged with said sleeve;
b) charging catalyst to the reaction zones;
c) flowing fluid reactant through the first fluid conduits, the chambers, and through the fluid permeable structures attached to the sleeves and into the reaction zones to contact the catalyst therein and form reaction mixtures;
d) flowing the resulting effluents through the fluid permeable ends of the reactor inserts and removing the effluents through the second fluid conduits; and
e) analyzing the effluents.

24. The process of claim 23 wherein the fluid reactant is flowing through the first fluid conduits at a superficial velocity sufficient to fluidize the catalyst in the reaction zones.

25. The process of claim 23 further comprising determining the superficial velocity sufficient to fluidize the catalyst in the reaction zones by ramping the superficial velocity of the of the fluid reactant flowing through the first fluid conduits while monitoring the conversions achieved by the catalysts in the reaction zones; plotting the superficial velocity versus conversion and graphically analyzing the plot in order to define a range of superficial velocities which fluidize the catalysts.

26. The process of claim 23 wherein the fluid reactant is flowing through the first fluid conduits at a superficial velocity sufficient to maintain the catalyst in the reaction zones in a fixed bed.

27. The process of claim 23 wherein the fluid reactant flowing through the first fluid conduits is at a superficial velocity sufficient to maintain the catalyst in the reaction zones in a fixed bed for a period of time and at a superficial velocity sufficient to maintain the catalyst in the reaction zones in a fluidized bed for a period of time.

28. The process of claim 23 further comprising an inert fluid flowing through the first fluid conduits at a superficial velocity sufficient to fluidize the catalyst in the reaction zones.

29. The process of claim 23 further comprising analyzing the effluents periodically over time.

30. The process of claim 23 further comprising sampling the effluents prior to analyzing the effluents.

31. The process of claim 23 further comprising simultaneously sampling the effluents prior to analyzing the effluents.

32. The process of claim 23 wherein the effluents are analyzed by an analytical technique selected from the group consisting of chromatography, spectroscopy, nuclear magnetic resonance, and combinations thereof.

33. The process of claim 23 further comprising preheating the fluid reactant prior to passing through the fluid permeable structures attached to the sleeves and into the reaction zones.

34. The process of claim 23 further comprising measuring the temperature in the reaction zones.

35. The process of claim 23 further comprising calculating from the results of the analysis of the effluent a variable selected from the group consisting of activity, selectivity, yield, or a combination thereof.

36. The process of claim 35 further comprising comparing the catalysts contained in the plurality of reactors on the basis of the activity, selectivity, yield, or a combination thereof.

37. A process for evaluating the performance of multiple catalysts comprising
  a) providing an apparatus comprising:
    i) a well having an open end and a closed end;
    ii) a first seal retained by said flanged open end of said well;
    iii) a sleeve having a top end, a bottom end, and a cross-section, said bottom end inserted within said open end of the well;
    iv) a fluid permeable structure attached to said sleeve at least partially spanning the cross-section of said sleeve and defining a chamber between said closed end of the well and said fluid permeable structure attached to said sleeve;
    v) a reactor insert having a fluid permeable end and a upper end containing a first and a second fluid conduit, said fluid permeable end inserted within said top end of said sleeve forming a reaction zone between said fluid permeable structure attached to said sleeve and said fluid permeable end of said reactor insert, said upper end of the reactor insert engaged with said first seal, said first fluid conduit in fluid communication with said chamber; said second fluid conduit in fluid communication with said fluid permeable end of said reactor insert; and
    vi) a second seal retained by said reactor insert and engaged with said sleeve;
  b) charging catalyst to the reaction zones;
  c) flowing fluid reactant through the second fluid conduits, through the fluid permeable ends of the reaction inserts and into the reaction zones to contact the catalyst and form reaction mixtures;
  d) flowing the resulting effluents through the fluid permeable structure attached to the sleeves, through the chambers and removing the effluents through the first fluid conduits; and
  e) analyzing the effluents.

38. The process of claim 37 further comprising analyzing the effluents periodically over time.

39. The process of claim 37 further comprising sampling the effluents prior to analyzing the effluents.

40. The process of claim 37 further comprising simultaneously sampling the effluents prior to analyzing the effluents.

41. The process of claim 37 wherein the effluents are analyzed by an analytical technique selected from the group consisting of chromatography spectroscopy, nuclear magnetic resonance, and combinations thereof.

42. The process of claim 37 further comprising measuring the temperature in the reaction zones.

43. The process of claim 37 further comprising calculating from the results of the analysis of the effluent a variable selected from the group consisting of activity, selectivity, yield, or combinations thereof.

44. The process of claim 43 further comprising comparing the catalysts contained in the plurality of reactors on the basis of the activity, selectivity, yield, or combinations thereof.

45. A process for evaluating the performance of multiple catalysts comprising:
   a) providing a plurality of reactors each comprising:
      i) a well having an open end and a closed end;
      ii) a first seal retained by said flanged open end of said well;
      iii) a sleeve having a top end, a bottom end, and a cross section, said bottom end inserted within said open end of the well;
      iv) a fluid permeable structure attached to said sleeve and spanning at least a portion of the cross section of the sleeve and defining a chamber between said closed end of the well and said fluid permeable structure attached to said sleeve;
      v) a reactor insert having a fluid permeable end and a top end containing a first and a second fluid conduit, said fluid permeable end inserted within said top end of said sleeve forming a reaction zone between said fluid permeable structure attached to said sleeve and said fluid permeable end of said reactor insert, said top end of the reactor insert engaged with said first seal, said first fluid conduit in fluid communication with said chamber; said second fluid conduit in fluid communication with said fluid permeable end of said reactor insert; and
      vi) a second seal retained by said reactor insert and engaged with said sleeve;
   b) charging catalyst to the reaction zones;
   c) flowing fluid reactant through the first fluid conduits, the chambers, and through the fluid permeable structures attached to the sleeves and into the reaction zones at superficial velocity sufficient to maintain the catalyst in the reaction zones in a fluidized bed mode, to contact the catalyst therein and form reaction mixtures, flowing the resulting effluents through the fluid permeable ends of the reactor inserts and removing the effluents through the second fluid conduits and analyzing the effluents; and
   d) flowing fluid reactant through the second fluid conduits, through the fluid permeable end of the reaction inserts and into the reaction zones at the same superficial velocity as in act (c) to contact the catalyst and form reaction mixtures and flowing the resulting effluents through the fluid permeable structures attached to the sleeves, through the chambers and removing the effluents through the first fluid conduits and analyzing the effluents;

where (c) and (d) are carried out in any order.

* * * * *